United States Patent [19]

Glaser

[11] Patent Number: 5,081,871
[45] Date of Patent: Jan. 21, 1992

[54] BREATH SAMPLER

[75] Inventor: Robert A. Glaser, Cincinnati, Ohio

[73] Assignee: The United States of America as represented by the Secretary of the Department of Health and Human Services, Washington, D.C.

[21] Appl. No.: 659,490

[22] Filed: Feb. 25, 1991

Related U.S. Application Data

[63] Continuation of Ser. No. 463,574, Jan. 11, 1990, abandoned, which is a continuation-in-part of Ser. No. 305,286, Feb. 2, 1989, abandoned.

[51] Int. Cl.$^5$ .................................................. A61B 5/00
[52] U.S. Cl. ................................. 73/863.23; 128/719; 422/84
[58] Field of Search ........... 73/863.02, 863.12, 863.21, 73/863.23, 863.25, 864.51, 863.31, 23.3; 422/83–85, 88, 89, 92; 55/270; 128/719, 730; 29/213.1, 221.6

[56] References Cited

U.S. PATENT DOCUMENTS

| | | |
|---|---|---|
| 2,484,217 | 10/1949 | Gardenier ............................ 128/719 |
| 2,795,223 | 6/1957 | Stampe .................................. 422/84 |
| 3,509,771 | 5/1970 | Moberg et al. . | 
| 3,600,134 | 8/1971 | Noller ................................... 422/84 |
| 3,676,073 | 7/1972 | Luckey ................................. 422/84 |
| 3,746,512 | 7/1973 | Kamei et al. ......................... 422/84 |
| 3,858,573 | 1/1975 | Ryan et al. . |
| 3,910,261 | 10/1975 | Ragsdale et al. . |
| 4,080,170 | 3/1978 | Borkenstein ........................ 422/84 |
| 4,090,078 | 5/1978 | Heim ..................................... 422/84 |
| 4,130,487 | 12/1978 | Hunter et al. ........................ 55/274 |
| 4,346,584 | 8/1982 | Boehringer ..................... 73/863.02 |
| 4,710,206 | 12/1987 | Allen et al. ............................. 55/74 |

FOREIGN PATENT DOCUMENTS 0153741 9/1985 European Pat. Off. ............ 128/719

OTHER PUBLICATIONS

Glaser et al., "Direct Sampling of Organic Solvents in Expired Breath with a New Solid Sorbent Sampling Device", Scand. J. Work Environ Health, 14 (1988).
Morgan et al., "Design and Laboratory Evaluation of Breath Sampling Respirator for Organic Solvent Biological Monitoring", Appl. Ind. Hyg., vol. 3, No. 2, Feb. 1988.
Glaser et al., "Investigation of Charcoal Cloth as a Sorbent for Integrated Sampling of Solvent Vapors in Mixed-Expired Breath Using a New SS Sampler", Am. Ind. Hyg. Assoc. J., Feb. 1989.
Article Entitled, "Comparison of Three Sampling and Analytical Methods for Measuring m-Xylene in Expired Air of Exposed Humans", by Glaser et al., Am. Ind. Hyg. Assoc. J. 51(3):139–150 (1990).

Primary Examiner—Robert Raevis
Attorney, Agent, or Firm—Lowe, Price, LeBlanc & Becker

[57] ABSTRACT

An apparatus for sampling volumetric quantities of human exhaled breath has three conduits and may be provided in "Y" or "T" shaped configuration. The free end of one of the conduits is adapted to connect with the mouth of the subject being tested. Another of the conduits is adapted to pass ambient air to the subject, this conduit being provided with a suitable filtering mechanism such as a charcoal inhalation canister and an inlet check valve. The third of the three conduits supports an appropriate sampling canister for receiving exhaled breath from the subject, and this conduit also is provided with a one-way check valve. In another aspect of the invention, there is also provided a method for collecting a sample of exhaled breath from a subject to collect therefrom a selected analyte and to accurately quantify its presence in the subject's breath.

21 Claims, 12 Drawing Sheets

BREATH SAMPLER

FIELD OF THE INVENTION

This application is a continuation of application Ser. No. 463,574 filed Jan. 11, 1990, now abandoned, which is a continuation in-part of U.S. patent application 07/305,286 filed Feb. 2, 1989, now abandoned.

The present invention relates to methods and devices for measuring and analyzing contents of gas samples, and more particularly to a method and apparatus for sampling volumetric quantities of human exhaled breath, and then either performing on-site analyses for measuring volatile compounds present in the sampled volume of breath, or storing the sampled volume so that appropriate analyses can be performed at a later time.

BACKGROUND OF THE INVENTION

For nearly two decades, there has been a growing need for gas sampling devices capable of applications beyond the more typical uses, as for example achieving law enforcement objectives (e.g., breathalyzers) and achieving medical objectives (e.g., patient breathing assist). Indeed, since 1970 when OSHA was established, there has been an increased awareness of the need to continuously monitor conditions in the workplace to assure compliance with Federal and State regulations.

Since breath is the only biological fluid that may be obtained noninvasively and on demand, it is currently the matrix of choice for a number of applications as for example in law enforcement and medical evaluation such as breathanalyzers and patient breathing assist. These uses generally rely on the fact that the concentration of the analyte of interest is in very high concentrations such as ethanol or carbon dioxide and can be analyzed with instrumentation that does not require separation of the analyte from other interferents.

Initial attempts at collecting exhaled breath samples for analyses of volatile substance content involved the use of two types of apparatus, namely the glass sample tube and the gas sampling bag. The glass sample tube permitted only a limited sample volume to be collected, and its use was short-lived. On the other hand, the gas sampling bag enjoyed a far longer usefulness for this purpose. Nevertheless, this apparatus has its shortcomings as well, and for those reasons its use also is inherently limited. Most significant among the objections is that in most circumstances the bag becomes bulky after sample collection and must be almost immediately transferred to a laboratory in order that desired analyses can be performed.

Furthermore concentration of a gas component using an absorbent is generally not feasible when using such gas collection containers and, therefore measuring an analyte in large volumes of exhaled breath that are contributed over a long period of time is not practical.

For the purposes of this art, two different breath samples can be taken, namely a "mixed" and an "end" or alveolar breath sample. A solvent in the deep lung or alveolar region of the lung is in intimate contact with solvent in the bloodstream. If a sample of solvent in the deep lung air is obtained that sample will be referred to as an alveolar or end-expired sample. As the solvent is exhaled, the sample becomes diluted with air in the upper respiratory track and is known as a mixed-expired sample. Generally an alveolar sample is regarded as being indicative of bloodstream solvent concentrations since that sample is in intimate contact with solvent in the blood stream. The manual technique for end-expired sampling requires the subject to hold his breath for about 20 seconds then to exhale, discarding the first 30–50% of the sample; and finally collecting the end-expired portion of the sample with the sampling device. There are also automated techniques for sampling end-expired air.

The concentrations of solvents in an exhaled breath sample are normally very low. Therefore, it has been found necessary to have the analytes in the bag sufficiently concentrated on an appropriate sorbent prior to analysis. In addition, if the analytes are stored in the bag for extended periods, severe losses of analyte may occur by absorption of the analyte into the bag wall or permeation of the analyte through the bag wall. In using the gas sampling bag, it has become apparent that concentration of the analytes on solid sorbent material is generally not feasible in the field. The only technique for concentrating the contents of the bag is via indirect means. The sample must first be trapped in the bag. A solid sorbent sampler is then connected at one end to the bag and the other end to a pump. A known volume of air in the bag is then sampled. Thus outside of the laboratory, neither the gas sampling bag nor the glass sample tube has been found to facilitate either direct concentration to volatile analytes in the samples taken or storage of the taken samples for extended periods of time.

Subsequently, other devices have been developed for sampling volumes of exhaled breath. For example, Boehringer et al. U.S. Pat. No. 4,046,014 discloses a charcoal tube sampler device for sampling respiratory gases in alveolar air. Another sampling device, which employs changes in pressure or flow rate in a main gas flow tube to initiate the sampling process as well as to terminate it, is disclosed in U.S. Pat. No. 4,297,871. Still another gas sampling device, disclosed in Ryan et al U.S. Pat. No. 3,858,593, incorporates a cylindrical alveolar gas trapping device having check valves at opposite ends which are openable upon application of exhalation pressure, and a side wall valved access tube for selective removal of the trapped gas from within the cylinder to a gas analyzer. Each of these subsequently developed devices also suffer disadvantages which make them undesirable for use. In particular, there is no provision for continuous mixed-expired sampling or filtering of inhalation air, and no provision for storing the collected gas sample for analysis at a subsequent time.

OBJECTS OF THE INVENTION

It is therefore an object of the invention to overcome deficiencies in the prior art, such as indicated above.

It is a further object of the present invention to provide improvements in analysis and in gaseous sampling.

It is another object of the present invention to provide a breath sampling device capable of sampling trace amounts of compounds in large volumes of human breath for analysis by conventional gas analyzer apparatus or other analytical procedures to determine the presence of trace levels of volatile compounds.

It is still another object of the invention to sample trace analytes using a layered sorbent sampling scheme. For example, high molecular weight analytes are collected on the first layer of the sampling stack using a carbon-type sorbent. Low-molecular weight compounds pass through the first stage and are collected on the second or tertiary stage using a sorbent such as molecular sieves.

It is still another object of this invention that the sidestream port may be used for purposes other than sampling. For example, in order to count the number of breaths, the port may be connected to a pressure sensor that converts positive or negative pressure impulses into a signal that is registered by a counter.

It is still another object of the invention to provide a mainstream- or sidestream sample canister that can be desorbed by solvents or thermal desorption techniques or by supercritical fluid extraction.

Yet another object of the invention is to provide a breath sampling device capable of collecting mainstream samples or sidestream samples using sorbents. Suitable activated charcoal-based sorbents include any activated natural charcoal as well as synthetic charcoals. An example of a natural charcoal is coconut-based charcoal. Examples of synthetic charcoals include activated charcoal cloth, activated petroleum or coal based charcoals, and other activated carbons which are commercially available such as Carbotrap ®, Carbosieve ®, and Carbopack ®. Suitable inorganic sorbents include the molecular sieves (synthetic or natural zeolites), silica gel and diatomaceous earth sorbents. Suitable synthetic resin sorbents include porous polymers such as Tenax ®, XAD-2 ®, the Porapak ® series polymers (e.g. Porapak S). and the Chromosorb ® series polymers (e.g. Chromosorb 101).

Another possible collection technique for both mainstream and sidestream sampling is to use a reagent-coated sorbent where the reagent reacts with the exhaled analyte to form a stable derivative. For example low-molecular weight aldehydes can be sorbed by contact with 2-(hydroxymethyl)piperidine-coated XAD-2. The unstable aldehydes are converted to oxazolidine derivatives which are stable and can be stored for later analysis.

Yet another object of the invention is to provide a breath sampling device capable of sidestream monitoring of the breath concentrations using suitable detection means such as a mass-spectrometer for breath-by-breath measurements of the relevant analytes. No technique other than a face mask previously permitted such monitoring in a contaminated environment.

Yet another object of the invention is to obtain a multi-breath sample. In this case the exhaled breaths are all passed through the same adsorbent bed so that the analyte from all the breaths are sorbed. This permits the measurement of very dilute concentrations of analyte which are sorbed from large volumes of breath over extended sampling periods.

Still another object is to provide a breath sampling device having alternative configurations which permit the collection of sidestream or mainstream samples, which facilitate purification of inhaled air or use a predetermined breathing gas source such as pressurized air, and which enable collection of the samples without use of a facemask.

Yet a further object is to provide a breath sampling device having almost no plastic components, other than a mouthpiece and an inlet check valve diaphragm, with which the breath sample comes in contact. However, the sampler could be made from PTFE (Teflon ®) or any plastic which has minimal capacity to absorb solvents.

Still a further object of the invention is to provide a unified sampler which can be used for both mixed and alveolar breath sampling.

It is still another object of the present invention to provide a system whereby collected samples of breath analytes can be analyzed at any convenient time, for example immediately on-site or after shipment of sorbent canisters to a laboratory having sophisticated equipment.

Yet another object is to provide a breath sampling device capable of being heated so that condensation of water vapor and analyte are prevented.

Yet another embodiment of the invention is to test a subject in the presence of contaminated air by not filtering the inhaled air. By measuring the amount exhaled, one can determine the amount or percent absorbed by the subject and thereby determine the dose received.

The invention is applicable to a number of situations where monitoring one's breath may be desirable in accordance with the invention. These include:

a. Control of substance abuse by determination of the concentration of volatile solvents or other materials that are present in the breath such as alcohol or toluene from inhalation of paint thinner vapors or glue sniffing.

b. Measurement of volatile compounds such as oral antiseptics in support of advertising efficacy claims by cosmetic manufacturers. Similarly, volatile compounds in the breath that are present from smoking, such as nicotine, may be measured for smoking-cessation or for other research purposes.

c. Measurement of trace levels of endogenous compounds in the breath that may be markers of a disease state such as breath acetone in diabetes.

d. Measurement of volatile endogenously-produced or used compounds such as carbon dioxide, oxygen or various other metabolites.

e. Monitoring workers or residents in the vicinity of hazardous areas, especially wastesites, for uptake of toxic chemicals.

f. Estimation of blood concentrations of absorbed organic solvents and of the volatile metabolites of these compounds that are excreted in the breath.

g. Measurement of natural air gasses which are not metabolically used or produced such as nitrogen to provide internal controls and comparisons.

h. Support of breath-based biological exposure indices (BEI,s) for control of worker exposure to hazardous compounds, especially solvents. The BEI's establish maximum concentrations for hazardous compounds in the various biological fluids. As such, this approach is superior to environmental monitoring of worker breathing zones to assure compliance with current State and Federally-mandated concentration standards. Breath based BEI's have been promulgated by the American Conference of Governmental Industrial Hygienists since 1981, and recognize that adsorption of hazardous chemicals by workers is quite variable due to dermal exposure and to ergonomic differences that affect individual ventilation rates. The breath based BEI's to be supported by this invention may rely on either or both mixed and alveolar sampling. The Federal Republic of Germany currently has standards for maximal levels of chemicals in the breath of exposed workers.

Generally, these situations demand that the sample be stored for later analysis by sophisticated separation technology and analytical techniques. In addition, the analyte concentration is expected to be very low because the sample may be collected hours after exposure or it may be present in only trace amounts. For example breath levels of such analytes are measured in the parts-per-billion to parts-per-million range. In order to accurately measure such levels and to establish standards to deal with such small amounts, a breath sampling technique should permit concentration of the analyte. In addition, the device should be compact enough to allow shipment to the laboratory for analysis if on-site analysis is not performed.

The above and other objects and the nature and advantages of the present invention will become apparent from the following detailed description of certain specific embodiments taken in conjunction with the drawing, wherein:

DETAILED DESCRIPTION OF THE INVENTION

Figure 3:
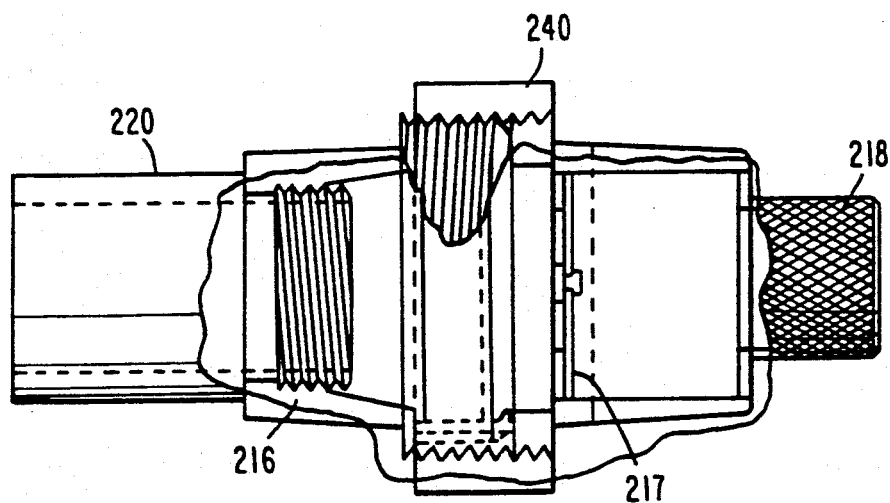
FIG. 3 is a detailed schematic illustration of a modification of the sampling device configuration shown in FIG. 2.

Referring now to the drawing, it will be understood that while the present invention may be embodied in a variety of configurations, for purposes of illustration two configurations will be discussed below, namely a "y" configuration and "T" configuration, as well as a variation of the latter. All of these configurations can be used for different types of sampling, although a particular configuration may provide advantages relative to a particular type of sampling. Thus, the "y" configuration shown in FIG. 1 minimizes the void volume as much as possible within manufacturing tolerances, thereby minimizing rebreathing of partially delivered samples from the void volume of the sampler device. The "T" configuration shown in FIG. 2 enables collection of both mixed-expired and end-expired samples using a single collection canister. The variation of FIG. 3 is primarily intended for single breath end-expired sampling, although it can also be used for single breath mixed-expired sampling. For all these configurations, the present invention contemplates that, subsequent to collection of the breath sample, analysis of the analytes contained in the collection canister will be made with conventional analysis equipment.

Figure 1:
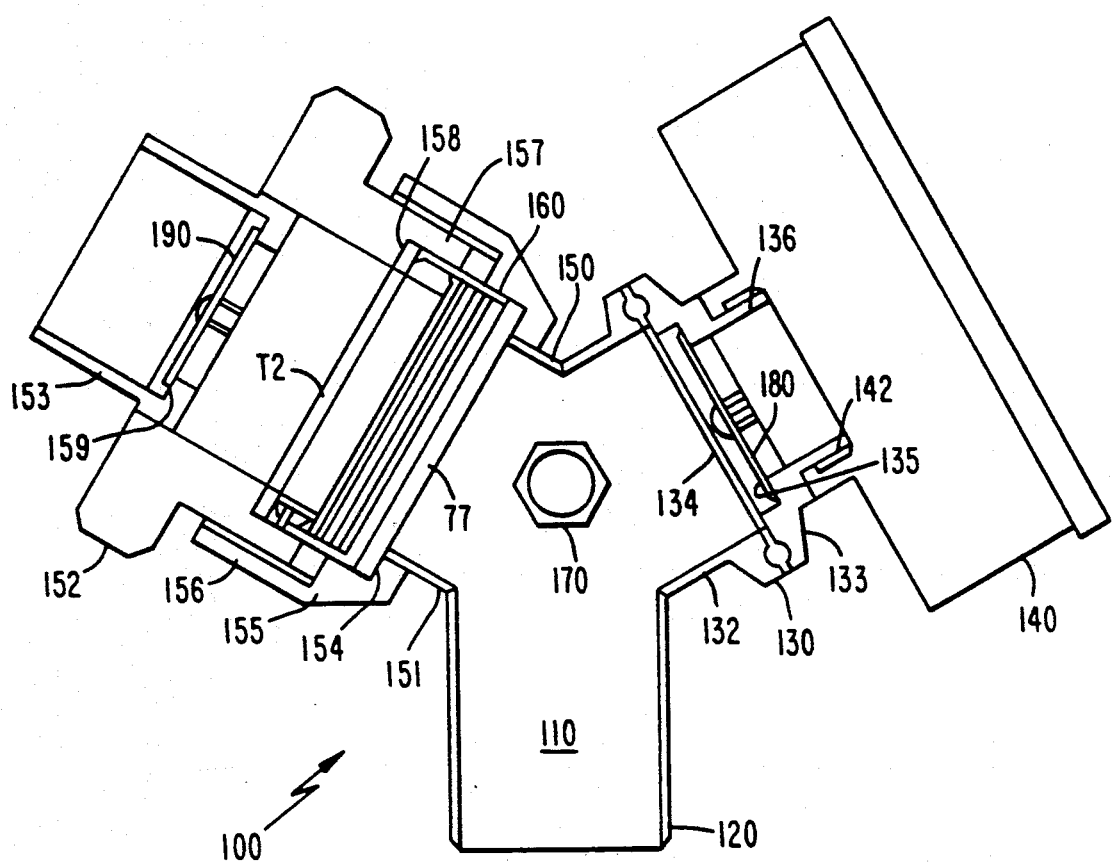
FIG. 1 is a detailed schematic illustration of a first configuration of the sampling device of the present invention.
Figure 2:
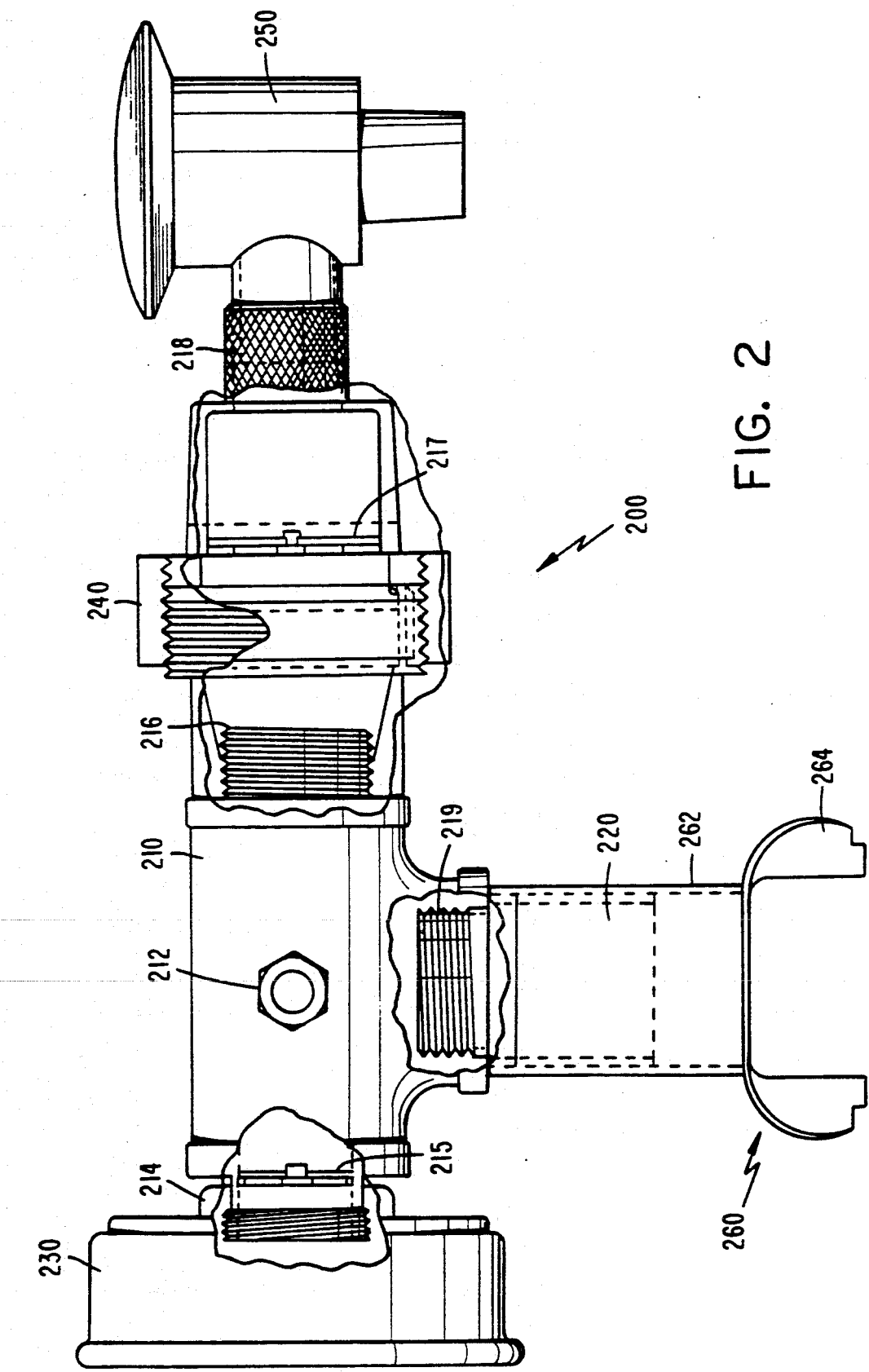
FIG. 2 is a detailed schematic illustration of a second configuration of the sampling device of the present invention.

Looking first at FIG. 1, the sampling device 100 involves a main body 110 having a tubular mouthpiece support portion 120 on which a bite wing mouthpiece, such as shown in FIG. 2, may be mounted, an inhalation canister support portion 130 for attaching a charcoal inhalation canister 140, a sample canister attachment portion 150 for attachment of a sample canister 160, and a sidestream port 170 for collection of sidestream samples. The port 170 is disposed substantially centrally of the main body and opens into the main body from one side thereof. Sidestream samples may be collected on sorbents contained in stainless steel or glass tubes attached to the port 170 via appropriate ferrules and fittings, or other similar mechanical connection means. The inhalation canister support portion 130 comprises a two part structure including a first tubular part 132 formed as an integral part of the main body and extending (i.e. having a longitudinal axis extending) at an angle of about 120° from the longitudinal axis of the tubular mouthpiece support portion 120. The first tubular part 132 includes an annular end face disposed in a plane perpendicular to the longitudinal axis of the first tubular part 132.

The inhalation canister support portion 130 also includes a second tubular part 133 having at one end an annular face matching the surface area and configuration of the end face of the first tubular part. The first and second tubular parts are secured to one another, with their annular end faces disposed in opposition to one another, via a clamp means. In effecting this connection, an annular gland or seal 134 is disposed and maintained between and spaces the end faces from one another. Various materials are effective for use as the seal; however, the preferred material is polytetrafluorethylene-covered silicone rubber.

The second tubular part includes an annular edge positioned forwardly of the clamped, sealed end faces, and the forwardmost end 136 of the second tubular part is provided with a threaded inner or outer surface 142 for making threaded engagement with a complementarily threaded outer or inner surface 142 on the charcoal inhalation canister 140, thereby insuring that the canister 140 is securely attached to the second tubular part. An inlet check valve 180, having a twofold function, is disposed on the annular ledge 135. The major functions of the inlet check valve 180 are: (1) to open under negative pressure (inhalation) thus permitting the user to inhale from the ambient through the inhalation canister 140; (2) to close under pressure and thereby prevent exhaled air from escaping from the main body of the sampler back through the inhalation canister 140; and (3) to direct the exhaled sample through a sample bed in section 160 of the sampler.

The sample canister support portion 150 includes a first canister housing part 151, a second canister retaining part 152 and a third housing part 153 for engagement of a volume measuring device (not shown, but to be discussed later). The first housing part 151 comprised a tubular member, formed integrally with the main body and having a longitudinal axis disposed at approximately 120° from the longitudinal axis of both the inhalation canister support portion 132 and the mouthpiece support portion 120, and an annular sleeve 155 attached at the forward end of the tubular member. Sleeve 155 is provided with a forward facing annular land 154 for retaining a first polytetrafluoroethylene (PTFE or "Teflon") gasket T1 and a forwardly extending annular cuff 156 bearing a set of internal threads.

Housed within sleeve 155 forwardly of the land 154 is a sample canister 160. Secured by threads within cuff 156 is the externally threaded, rearwardly facing, annular extension 157 of the canister retaining part 152. A second PTFE gasket T2 is supported on the forward facing land 150 of retaining part 152, and the sample canister is held securely between the PTFE gaskets T1, T2 within sleeve 155 when the retaining part 152 is threaded tightly in a rearward direction and within the sleeve 155. The housing part 153, secured within the forward end of retaining part 152 by a welded connection, comprises an annular sleeve member having a forwardly facing annular seat 159 at its rearward end. Disposed on, and secured to, the annular seat 159 is an outlet check valve 190 having a construction which is the same as that of inlet check valve 180.

The major functions of the outlet check valve 190 are as follows: (1) to close under negative pressure (inhalation) and prevent environmental contaminants from entering the sampler body; (2) to open under positive pressure (exhalation) and thereby permit the sample stream to pass through the sample bed in section 150 of the sampler; and (3) to direct the exhaled sample through the sample bed in section 160 of the sampler.

Each check valve 180, 190 comprises a one-way diaphragm-type valve with an integral cross-hatch support. Welded to the center of the support is a retainer bud for the valve diaphragm. The cross-hatch support is of the type known as a "low flow resistance" cross-hatch, is made of stainless steel, and is silver-soldered to a land at the respective inlet or outlet location. The purpose of the cross hatch support is to provide a retention foundation for the respective diaphragm valve during inhalation or exhalation.

FIG. 2 illustrates a second breath sampler device 200 exhibiting the "T" configuration described above which facilitates obtaining mixed expired breath samples. This second device includes a tubular main body 210 to which a stainless steel compression fitting 212 is secured (via welding) at an opening substantially centered in the tubular main body 210. The fitting 212 is provided to facilitate the collection of sidestream samples, and it is to be understood that the diameter of the fitting may be chosen as a function of the particular application or task to be accomplished. One side of the tubular main body 210 (hereinafter referred to as the "inlet" side) supports, via a first threaded connection means 214, an inhalation canister 230. An inlet check valve 215 is located downstream of the threaded connection means 214. Directly opposite the inlet side of the main body is the "outlet" side where the sampling canister 240 is located and supported on the main body via a second threaded connection 216. An outlet check valve 217 is positioned downstream of the second threaded connection. In FIG. 2, the inlet canister the mouthpiece support and the sample canister are shown attached to the sampler main body 210 by threaded connections. However, these connections could also be accomplished by use of alternative fittings e.g. tapered sleeve- or O-ring type slip fittings.

Typically, both the inlet and outlet check valve bodies are fabricated from stainless steel discs. A plurality of openings (four equiangularly spaced openings in the preferred embodiment) are provided in the discs to form an array which facilitates air flow through the discs. Retainer buds are welded directly to the center of the discs to assist in securing the silicone rubber diaphragms against dislodgement. On the downstream side of outlet check valve 217 is a knurled tapered connection 218 which connects directly to a respirometer 250 used to measure and record the volumes of exhaled breath. This connection has been made to facilitate connection to the respirometer; but other volumetric devices may be used by connecting them with suitable fittings and connections to the tapered connection 218. Through a third threaded connection 219, a tubular mouthpiece support portion 220 is coupled to the main body 210 of the sampler device. A bitewing mouthpiece 260 includes an elongated sleeve portion 262 adapted to be mounted over the tubular mouthpiece support portion 220, and a mouth engaging portion 264.

The mouthpiece support portion 220 may also be directly connected to the sampling canister 240, as seen in FIG. 3. This modification of the FIG. 2 configuration facilitates single-breath "end-expired" collection of samples. It should therefore be clear that both the "mixed-expired" sampling device shown in FIG. 2, and the "end-expired" sampling device shown in FIG. 3, are designed so that either one will fit with the same mouthpiece support portion. The support acts as the mouthpiece for the configuration shown in FIG. 3. In both of the FIG. 2 and FIG. 3 embodiments of the sampling device, the inlet and outlet check valves employed are substantially identical with those used in the sampling device of FIG. 1. Moreover, the sampling canister 240 used in the embodiments of FIGS. 2 and 3 is preferably substantially the same as that described above for use with the embodiment of FIG. 1.

Figure 14:
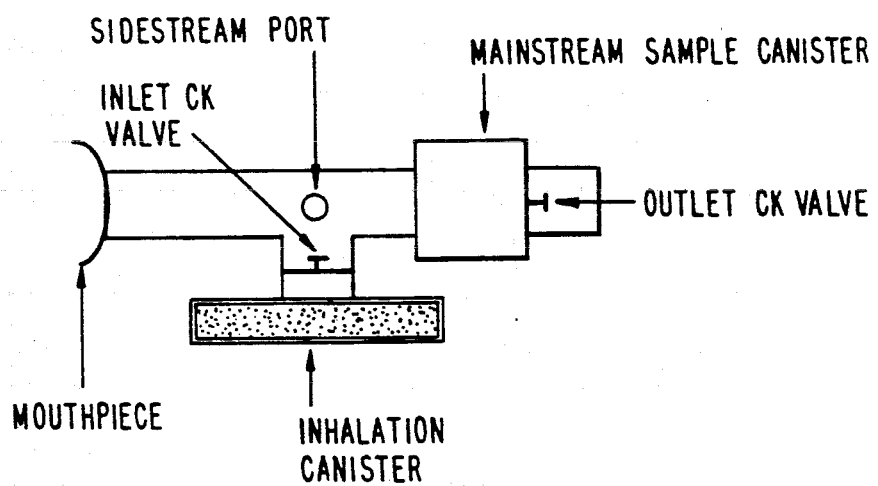
FIG. 14 is an "L"-shaped configuration of the sampler, which further minimizes void volume.

The design may be L-shaped as shown in FIG. 14. This embodiment minimizes sampler void volume and permits the sample canister to be directly in the path of the exhaled sample so that there are no angles which produce back pressure and turbulence which under certain circumstances may be undesirable.

Because of its construction, the y-configured sampler shown in FIG. 1 is particularly constructed for continuous mixed-expired breath sampling. The inhalation canister assembly 140 is attached to the main body of the sampler 110 via a Tri-clover clamp 134. This clamp permits the inhalation canister assembly to be removed from the main sampler body in order for the inlet check valve (180) to be replaced. Unless a single sampler is dedicated to each subject, the y design, as configured in FIG. 1, also requires that the sample canister (stack) be removed and stored immediately after sampling. This introduces the possibility of passive sampling of contaminants in the industrial environment by the charcoal cloth sorbent and may limit the reliability of the sample.

In order to avoid the use of the Tri-clover clamp, reduce fabrication costs and to make the sampler more flexible, the sampler shown in FIG. 2 was created. In that sampler the threaded inhalation canister support (214 of FIG. 2) is welded to the main body of the T, eliminating the need for a Tri-clover clamp and substantially reducing fabrication costs. A conventional stainless steel pipe "T" may be used as the main body of the sampler. In addition, this construction places the removable sampling cup in a canister that may be removed from the main body of the sampler and shipped off for analysis. This canister may also be directly attached to the respirometer via the tapered fitting 218 of FIG. 2. As configured in FIG. 2, the sampler permits continuous mixed-expired breath sampling (mainstream or sidestream) just as does the sampler in FIG. 1. However, when the sampler of FIG. 2 is disassembled and re-configured to the sampler of FIG. 3, single breath end-expired (or for that matter single breath mixed-expired) samples may be obtained.

In the sampler of FIG. 2, the inhalation canister support 214 cannot be separated from the main sampler body to permit loading of the inlet check valve. The outlet check valve 217 is in a deep, inaccessible chamber of the sample canister. Therefore, a means of loading the inlet check valve into the sampler body and the outlet check valve into the sample canister is desirable. That is the purpose of the loading tool shown in FIGS. 6 and 7. The use of this tool actually dictates the "T" configuration of the sampler in FIG. 2, or the L-shaped configuration in FIG. 18, because of the necessity to permit ready accessibilty of the check valve loading tool to the inlet check valve support through the opening at 216 in FIG. 2. However, a Universal Check Valve Loading Tool (see below) has been created to allow the inlet check valve to be loaded into a Y-shaped main body or an L-shaped main body that has no access port. Therefore, it is also possible to replace the T-shaped main body of the sampler in FIG. 2 with a lower void volume L-shaped or Y-shaped main body, while still retaining the flexibility of the T-shaped design. All that is required for this purpose is to machine the main sampler body from a Y-shaped pipe fitting or fabricate the body in an L-shape or to cast the body in a Y or L-shape.

In summary, the y, the L and the T configurations permit mixed-expired sampling. The particular Y design as shown in FIG. 1 permits only mixed-expired sampling because it is not shown with a removable sample canister and mouthpiece as is the T-shaped design of FIG. 2. However there is nothing intrinsic in the design of a Y-shaped sampler that would permit only mixed-expired sampling, e.g. the Y-shaped sampler of FIG. 1 can be easily adapted as noted above for obtaining single breath end-expired or mixed-expired samples.

Figure 4:
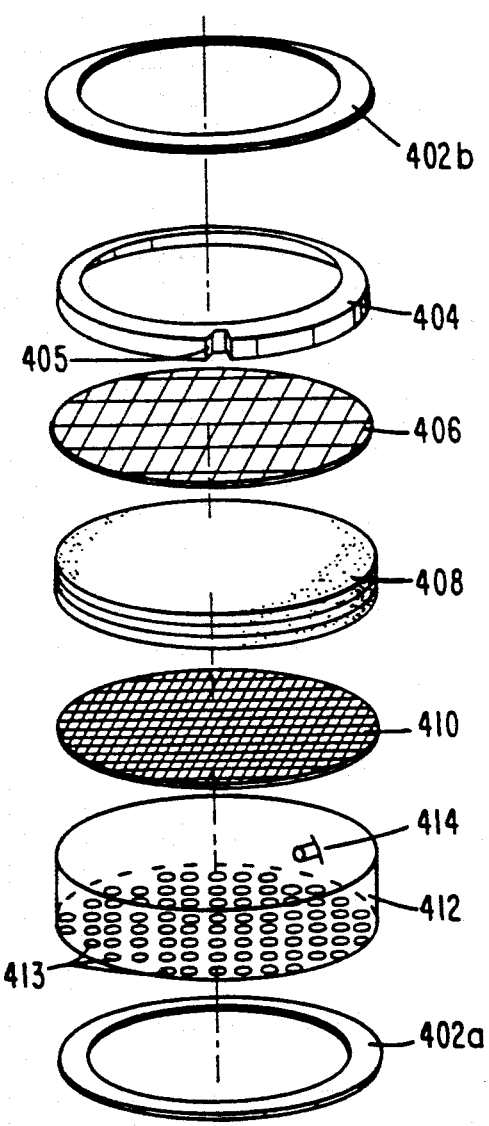
FIG. 4 is an exploded view of the components of one embodiment of the sampling canister contemplated for use with any of the embodiments of the sampling devices shown in FIGS. 1, 2, or 3.

FIG. 4 illustrates the structural elements contained within one embodiment of the sampling canister used in the present invention. PTF gaskets 402a and 4024' are positioned at the top and bottom of the stack elements. The gaskets provide a secure seal around the canister after it has been loaded into the sampler device. The sampling "stack" further includes a cylindrical toroidal weight or retainer 404, a first stainless steel retainer screen 406, charcoal cloth sorbent bed 408, and a second stainless steel retainer screen 410. The weight of retainer 404 retains sorbent bed 408 in the canister by compressing the first retainer screen 406 against bed 408. To prevent inhalation of sorbent fines, a second retainer screen 410 having a fine mesh is placed atop the array of openings 413 in the canister 412. The openings 413 preferably are provided in symmetrical array to form a grating.

The sampler canister 412 into which the stack of elements fits is designed to accommodate a large plurality of wafers of charcoal cloth of which the sorbent bed 408 is comprised (one embodiment contemplates element (11) wafers), including if necessary or desired, stainless steel screens for separating the adjacent sorbent wafers. An anti-rotation lug 414 is provided (e.g., via spot welding) on the interior of the annular wall of the canister. The lug 414 engages with the cutout 405 provided in the exterior annular surface of the toroidal weight 404 for preventing the weight from rotating the retainer screen 406 as the canister is being loaded into the sampler horsing. In this way, the sorbent bed is protected against being torn and the formation of fines during loading of the canister is prevented.

Figure 5:
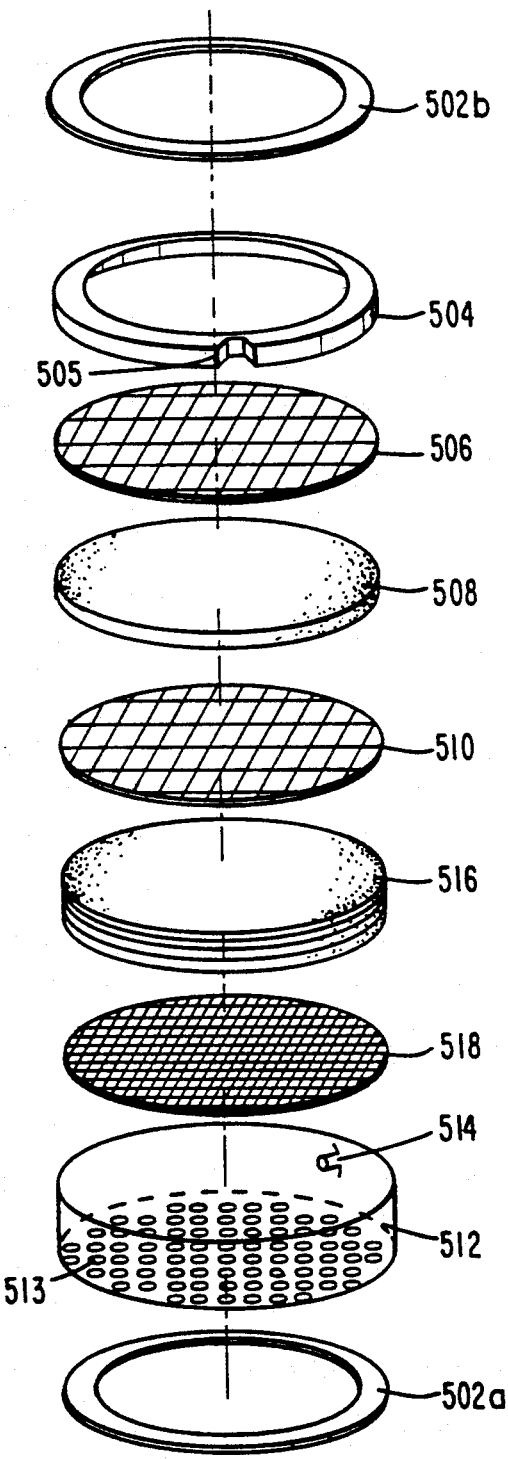
FIG. 5 is an exploded view of the components of a second embodiment of a sampling canister which can be used with any of the embodiments of the sampling devices shown in FIGS. 1, 2, or 3.

A second embodiment of the sampler canister, which is illustrated in FIG. 5, is contemplated for use with the embodiments of sampling devices shown in FIGS. 1, 2 or 3. This embodiment shows the use of charcoal cloth sorbents, although granular sorbents, such as silica gels or porous polymers could also be used. The canister comprises an assembly of elements including a toroidal shaped weight or retainer 504, a first retainer screen 506, a first sorbent bed 508, a second retainer screen 510, a second sorbent bed 516 and a third retainer screen 518. This assembly of elements is disposed within a stainless steel canister cup 512 having a bottom perforated with an array 513 of openings. An anti-rotational lug 514 is provided on the annular surface of the cup for engagement in the anti-rotational cutout 505 provided on the annular outer surface of the toroidal retainer 504.

As with the first embodiment of sampler canister illustrated in FIG. 4 and described above, two gaskets 502a, 502b' are positioned atop and below the sampler canister to provide a secure seal around the canister once it has been loaded into the sampler device. By using this second embodiment of the sampler canister, granular sorbents may be held in the cup 512 by the first, second and third retainer screens (506, 510 and 518, respectively), or by the u e of discs of very fine mesh stainless steel which are centered on, and soldered or welded to, a thin metal ring. Alternatively, the discs could be press-fit to and about the thin metal ring. Preferably, the outer diameter of the ring would be about equal to the inner diameter of the cup. Sorbents may be separated into front and back sections, and may be retained in place using the discs or the screens.

In the embodiments of the sampler device shown, the stainless steel canister cup may be eliminated from the canister housing or support member, and alternatively perforated discs of stainless steel may be welded to the inside of the canister housing or support member to form an equivalent cup base or bottom, and thereafter the sorbent beds and screens can be assembled to form the sampler canister.

In operation, the sampler devices shown in FIGS. 1 and 2 function in the same manner as a respirator mask. The subject (user), wearing a nose clamp and biting a bitewing mouthpiece, is instructed to breathe by mouth only. At the beginning of inhalation, negative pressure created inside the main body of the sampler closes the outlet or exhalation check valve and opens the inlet or inhalation check valve, thereby permitting fresh air to be drawn through the inhalation canister (140 in FIG. 1 and 230 in FIG. 2). When the subject exhales, the positive pressure created in the sampler main body forces the inlet check valve to close and the outlet check valve to open. Volatile compounds in the subject's breath are absorbed from the mainstream gas flow by the charcoal cloth sorbent medium or granular sorbent medium in the sample canister, or from the sidestream using other sorbents.

For collection of mainstream breath samples, exhaled volumes may be recorded using a Wright respirometer or other volumetric device (not shown). For sampling breath from the sidestream, the sample volume is recorded by multiplying the duration of sidestream sampling by the sidestream sampling flowrate, and then by a correction factor that accounts for the percent of time the subject spends exhaling. Laboratory studies have shown that such a correction factor is approximately 0.65. Other techniques to estimate sidestream sample concentration may also be used. Tests with volunteers have shown that sidestream carbon dioxide concentrations are approximately 71% of mainstream concentrations. Therefore, the sidestream sample concentration may be estimated by determining the mass sampled, dividing that mass by the volume sampled (i.e. actual sidestream flowrate x time), and then dividing that concentration by 0.71 to correct approximately to mainstream concentrations.

Either the mainstream, or the sidestream, mode of sampling permits large volumes of mixed-exhaled breath to be sampled without prior collection in and concentration from a gas-sample bag. In this way sufficient quantities of the absorbed compounds are permitted to be collected for analysis.

The check valves disclosed in each of the embodiments of the sampler device, i.e., the embodiments shown in FIGS. 1-3, can either be removable or non-removable. Non-removable valves could be secured, as by a press-fit or by welding, to their respective supporting structures. Removable check valves might be desirable where frequent cleaning of the valves is required, or where the contemplated cleaning process for the valves would not be practically carried out with the valves secured within their respective sampling devices.

While the outlet check valve has been shown in each of the embodiments to be placed in a specific location, it is possible to have the outlet check valve disposed in still other locations. For example it may be useful to place the outlet check valve upstream of the sampler canister. Without the sample canister attached the subject may flush his lungs free of environmentally-contaminated air for a prescribed period, by inhaling fresh purified air through the inhalation canister or other air source and venting the exhaled air to the atmosphere through the outlet check valve. Thereafter the sampler canister is attached to the sampler. The concentrations of the samples are then reflective only of bloodstream contamination levels and not of environmental contamination levels.

Figure 6:
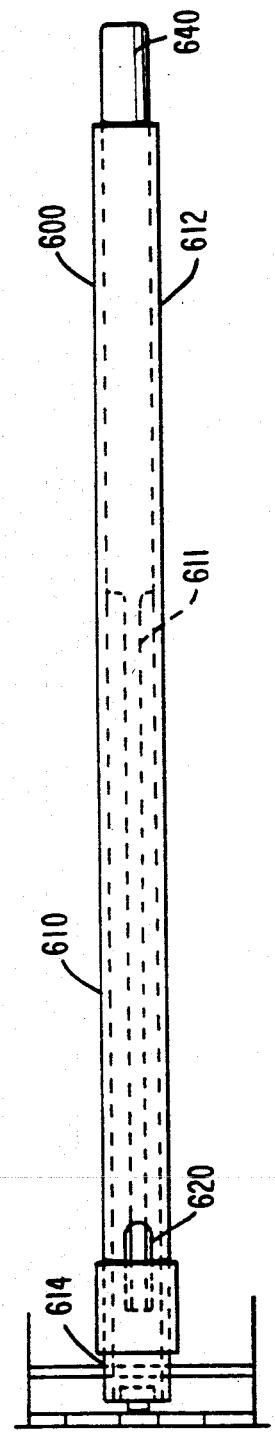
FIGS. 6 and 7 shown a tool which can be used to load the check valves used with the sampling devices of the present invention.
Figure 7:
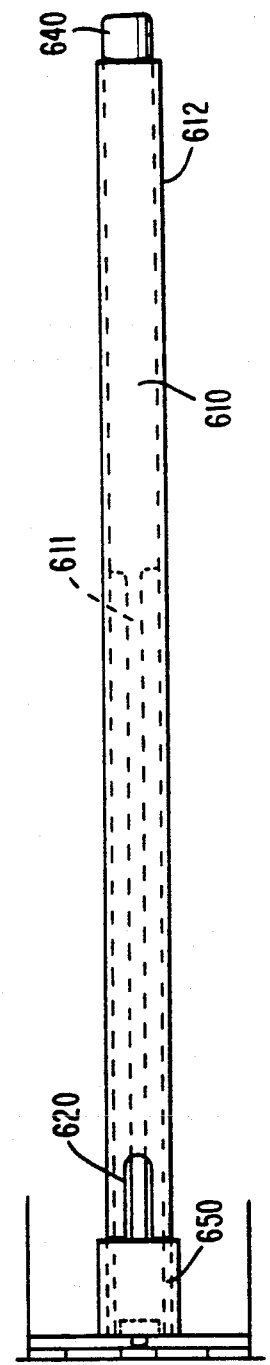

FIGS. 6 and 7 disclose a valve mounting tool, the use of which is for loading check valve diaphragms of the kind which can be removed from the sampler devices of the present invention. FIG. 6 illustrates the tool in a position in which a check valve has been inserted in preparation for mounting in a sampler device, while FIG. 7 illustrates the tool in a position in which the check valve has been mounted.

As shown in FIGS. 6 and 7, the tool 600 comprises an elongated guide tube 610 having a first push rod insertion end 612 and a second check valve supporting end 614. The length of the guide tube 610 is significantly greater than its diameter, and supports in its interior an elongated push rod 640. An elongated cutout or slot 620 extends, from a location adjacent the valve-supporting end 614 of the guide tube, along a short length of the guide tube in a direction towards the first end 612 thereof. A narrow strap of thin gauge metal 611 (preferably, stainless steel) is welded to one end of the push rod 640 which is inserted into and housed within the guide tube 610. Prior to insertion of the rod 640 into the guide tube 610, one free end of the strap is welded to the center of the circular peripheral edge surface of the one end of the push rod to lie adjacent to the longitudinal extent of the push rod. The other end of the strap further protrudes diametrically through the cutout and is welded to the inner annular surface of an outer sleeve member 650, which is disposed over and rides along the exterior of the guide tube 610.

In order to load the inlet or outlet check valves, the outer sleeve member 650 is moved rearwardly (to the right in FIGS. 6 and 7) over the guide tube 610 by the push rod 640. The check valve to be loaded is then pushed over the guide tube 610 and is retained in any suitable manner, e.g. the check valve can be made of a resilient or elastic material which deforms or rakes a friction fit with the guide tube.

The second end 614 of guide tube 610 is inserted into the inlet or outlet check valve mounting structure (in each of the sampler embodiments disclosed above) such that the guide tube is disposed over the retainer bud. The pushrod 640 is then pushed back through the guide tube 610 so that the outer sleeve member 650 engages the check valve and pushes it from the guide tube onto the retainer stem.

Removal of the check valve may be effected by using long stem tweezers, or some equivalent tool.

In the sampler devices described hereinabove, the exhaled volume of the mainstream sample is determined using an accurate volume measurement device, as for example a Wright respirometer. Volume measurements made are independent of the use of an inaccurate and imprecise technique e.g. collection of exhaled water on a high pressure-drop adsorbent, such as molecular sieves, where the amount of exhaled water collected must be assumed to be directly proportional to the volume exhaled.

The foregoing sampler devices permit sidestream, as well as mainstream, sampling. Sidestream sampling is important, and a capability for conducting this mode of sampling has been designed into the sampler devices of the present invention, for several reasons:

(1) Although the pressure drop associated with a charcoal cloth sorbent bed is low, subjects with respiratory problems may not be able to exhale through a sorbent bed.

(2) Sampling from the sidestream enables the user to employ sorbents that are selective to the collection and analysis of specific analytes. For example, research has indicated that alcohols are only poorly recovered from charcoal cloth, and it may thus be necessary to use sidestream sampling for collection of such analytes.

(3) The capacity of the charcoal cloth sorbent bed for high vapor pressure solvents such as methylene chloride may be limited. Sidestream samples can be collected at any desired flowrate on the sorbent of choice, such that problems with breakthrough are minimized.

(4) Multiple, and therefore replicate, samples may be obtained using the sidestream sampling option. One or more sorbents may be used to trap selective analytes at a variety of flowrates.

(5) The sidestream port enables the sampler to be connected to an appropriate continuous monitor for breath-by-breath measurements. In this manner, the sidestream port facilitates frequent and continuous analysis of breath samples which are uncontaminated by the analytes in the work environment.

(6) Pressure-sensors or flow-sensors may be connected to the sidestream port to measure the number of breaths and or the pressure/flow profile of each breath.

Figure 8:
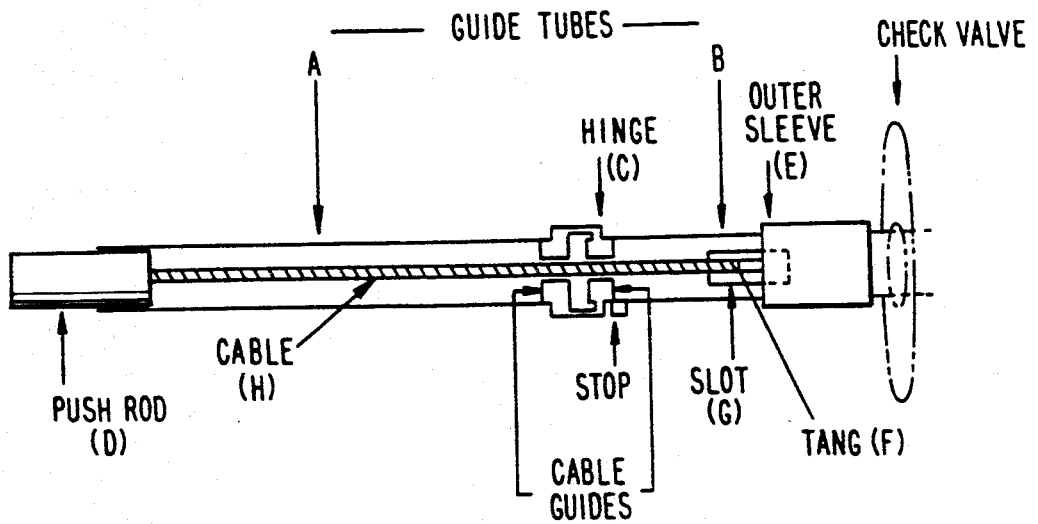
FIGS. 8 and 9 show another similar tool, FIG. 9 being a schematic view showing use of such tool in use.

In order to permit a low void volume Y-shaped design for the main sampler body that does not have a removable check valve assembly, it is necessary to employ a valve-loading tool as shown in FIG. 8 similar in function to that shown in FIGS. 6 and 7.

Figure 9:
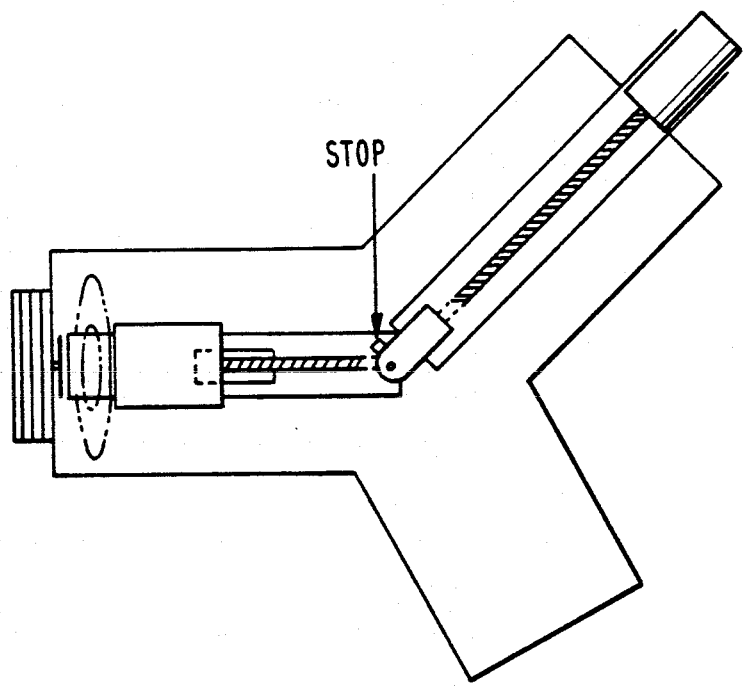

Referring to FIG. 8, two hollow cylinders (A) and (B) are used as guide tubes and are connected at a hinged joint (C). As configured, the two guide tubes (A) and (B) may be rotated relative to one another by approximately 120° in order to assure the proper angle of orientation of the tool relative to the retainer bud when the tool is inserted in the sampler body. However other angular orientations are also possible for example 90° for use with an L-shaped sampler that has no side access port. The hinge (C) must be relatively "stiff" and a positive "stop" may be attached to the guide tube (B) (see FIG. 9), in order to prevent the two guide tubes from being bent at an angle greater than 120° or other preferred angle relative to one another. The stop is a small metal stud welded to the body of tube (B), just above the hinge. The push rod (D) is a cylinder housed in a long (A) section of the guide tube. An outer sleeve (E) slides over the other (B) section guide tube and is welded to a short metal tang (F). A slot (G) has been cut into guide tube (B). The tang slips through the slot (G) inside of tube (B). A relatively stiff cable (H) connects the pushrod (D) to the tang (G). At one end, the cable is welded or press-fit to the push rod (D). At the other end, the cable is welded or pressfit to the tang (F).

The tool operates in the same way as the tool described in FIGS. 5 and 6. That is, the outer sleeve (E) is pulled back over the guide tube by pulling the push rod (D) back to the loading position. The check valve is then slipped onto tube (B). Section (B) of the tool is then inserted into the body of the sampler and forced up against the inner wall of the sampler body to bend the tool at the hinge (C) to approximately 120° or other preferred angle. The (B) section guide tube is then forced over the retainer but. The pushrod (D) is pushed, forcing the cable (H) through guide tubes (A) and (B), causing the outer sleeve (E) to slide along outside of guide tube B, thus pushing the check valve onto the check valve support. To improve functioning, inner cable guides as shown in FIG. 8 may also be used.

Figure 10:
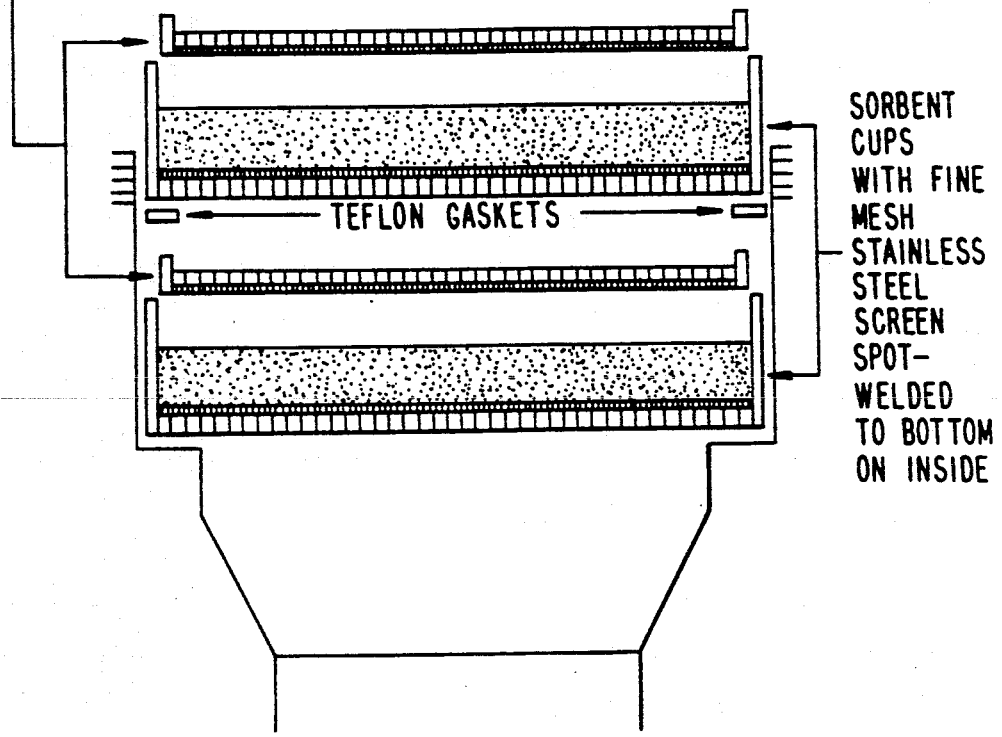
FIG. 10 is a schematic view of an improved sample canister for granular sorbents and/or combination of charcoal cloth and granular sorbents.

One embodiment of a sample canister for granular sorbents and for combinations of granular sorbents and charcoal cloth is shown in FIG. 10. In this configuration, the sorbent beds are retained in separate canisters of the type 512 shown in FIG. 5. Alternatively, this embodiment may also be used to retain several, e.g. primary, secondary and even tertiary, beds of charcoal cloth sorbent. However, in order to minimize pressure drops caused by large amounts of granular sorbent, it is preferred that the retainer cup not be as deep as that used for charcoal cloth sampling in previously discussed embodiments. The canisters are stacked atop one another as shown in FIG. 10. This arrangement permits a more positive seal of granular sorbent beds into the canister than are provided by those in the previous embodiments of FIGS. 4 and 5. There should be no possibility of granular sorbent from one sorbent section being accidentally mixed together with that of another sorbent section by spillage. Granular sorbent is retained in each of the cups by the fine-mesh stainless steel screens that are spot welded to the inside base of the cup (over the grating) and to the bottom of the heavy retainer grating.

These heavy retainer gratings serve to flatten the sorbent bed and thus prevent channeling during sampling. They essentially replace the toroidal weight of the previous embodiment. However, this construction does not include an anti-rotational lug in the sampler cup to engage a cut out on the heavy stainless steel grating as with the previous embodiment. Granular sorbents require a very tight seal to be held in place. The sorbent may be blown or fall out of the sampler past such an opening. Essentially, this is a cup-in-a-cup design. It may also be desirable to ensure that the individual sorbent beds be separated or sealed by Teflon gaskets as shown in FIG. 10.

Figure 11:
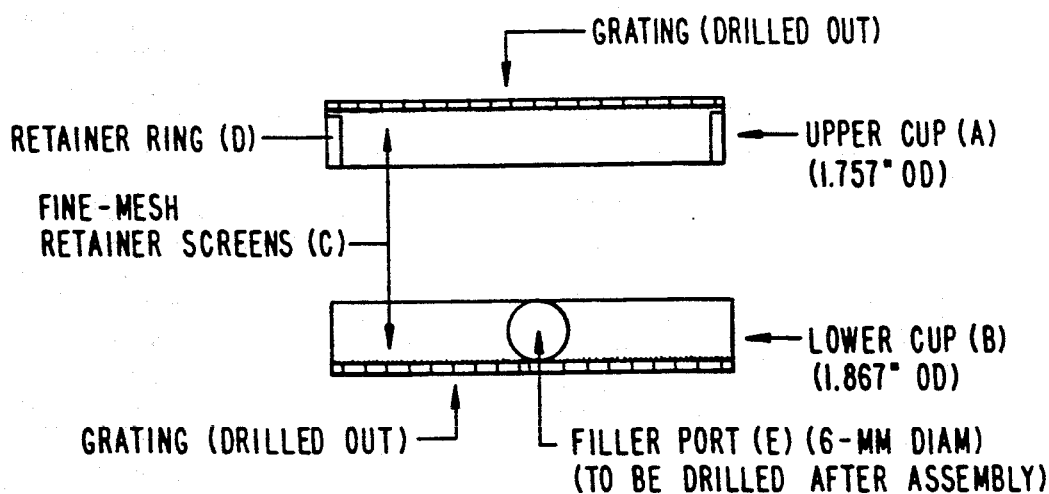
FIG. 11 is a schematic view of another improved sample canister for granular sorbents.

Alternatively, the granular sorbents may be used with a canister such as that shown in FIG. 11, this canister has also been fabricated from two stainless steel cups, an upper (A) and a lower (B). The outside diameter of the upper cup is approximately equal in the inside diameter of the lower cup. Fine-mesh retainer screens (C) (diameter=internal diameter of the upper cup) have been spot-welded over the grating in the inside of both cups. In addition, a retainer ring (D) has been press fit into the upper cup as shown. The entire upper assembly is then inverted and press-fit into the lower cup. Once press-fit together the two cups A and B, are permanently affixed to one another. The granular sorbents may be added or removed from the canister from a port (E) that is drilled into the side of the assembled canister. The hole may be threaded. This port is plugged with a threaded metal plug or a small plug of silanized glass wool or a teflon plug once the canister has been filled with sorbent. Dimensions are as shown in FIG. 11.

Figure 12:
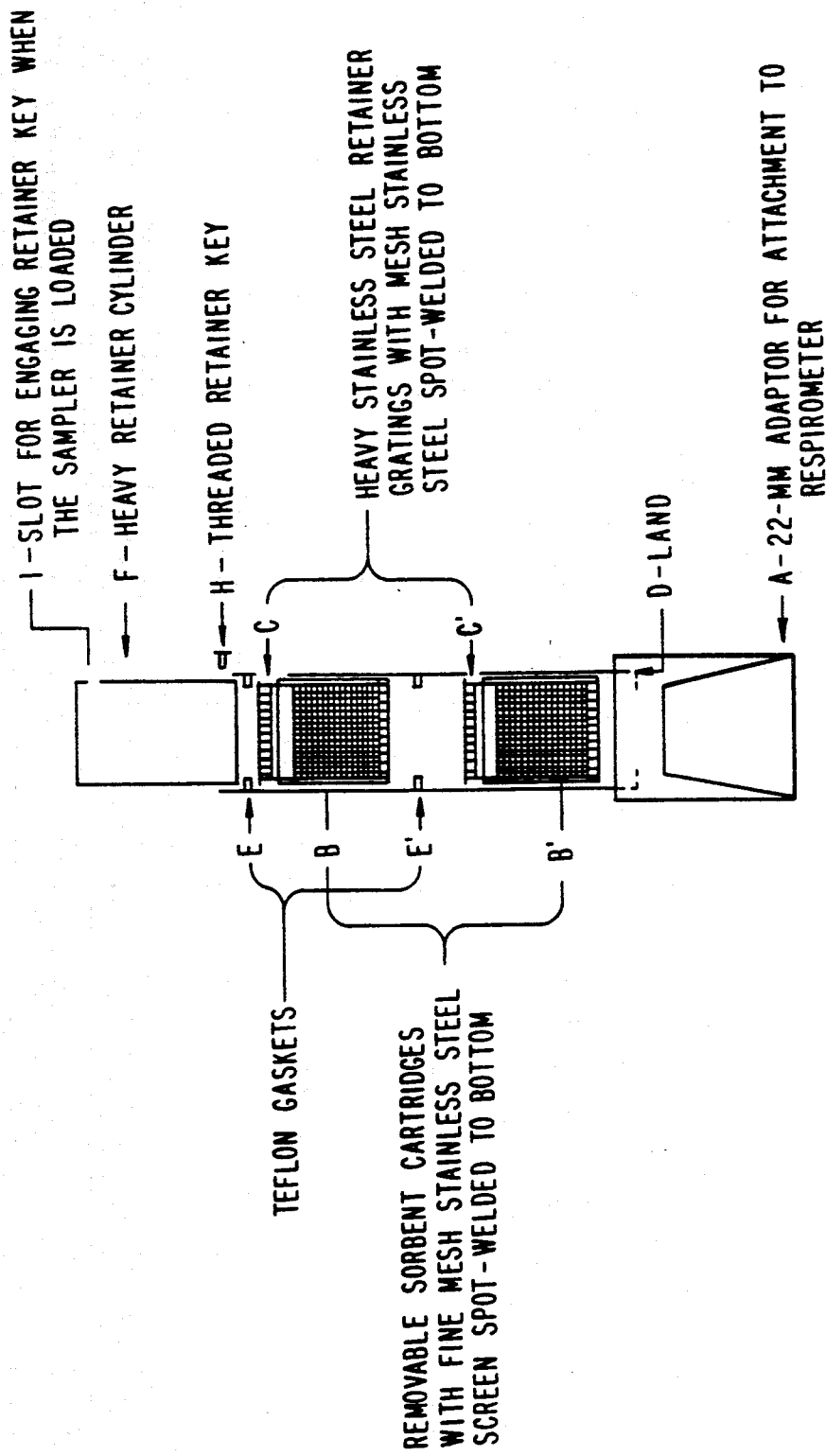
FIG. 12 is a schematic view of another alveolar sampler using granular sorbents.

Along these same lines, another embodiment is shown in FIG. 12 for another alveolar sampler which also employs granular sorbents. This device is primarily intended for sampling extremely low concentrations of solvents in alveolar breath. Samples of alveolar air collected with the device are primarily intended to be analyzed by thermal desorption. Thermal desorbers are commercially available and used extensively in environmental monitoring. For sampling, stainless steel or glass tubes, generally ranging in diameter from 0.25" to 0.625" are loaded with a sorbent. The manual breath sampling technique is used with this device. The subject exhales the end portion of the breath sample into the sorbent bed. The contaminants present in the air are trapped on the sorbent. The tube is capped and returned to the laboratory for analysis. During analysis, the tube is inserted into the thermal desorber where it is heated under a stream of inert gas such as nitrogen. This flushes the trapped solvent(s) from the sorbent into a gas chromatograph where it is analyzed. The major advantage of thermal desorption is that all of the solvent is removed from the sorbent bed by the thermal desorption process, and injected into the chromatograph for analysis. This contrasts with solvent desorption where the sample is diluted with solvent and only a very small portion of the sample is injected into the analytical instrument. Thus, thermal desorption significantly enhances sensitivity relative to solvent desorption and permits the analysis of much lower quantities of analyte than would be possible for analysis by solvent desorption.

The sampler of FIG. 12 described below is adapted for use with a 0.625" O.D. ×0.579" I.D. ×7.0" long stainless steel thermal desorption tube, i.e. the type that is used with a Tekmar ® thermal desorber. The solvents present in the breath are sampled on beds of a porous polymer such as Tenax ®; however, many other sorbents including charcoal cloth may be used for this purpose. This device is primarily intended to be used where the concentration of sample in alveolar breath is very low. Again, both front and back absorbing sections are used. The device is configured similarly to the granular sample canister shown in FIG. 10. The 0.625" OD thermal desorber tube is welded as shown to a 0.866" (22-mm) tapered adaptor (A), to form the main body of the sampler. The tapered adaptor permits ready attachment of the sampler to a Wright respirometer. The sorbent is retained in primary and backup stainless steel cartridges (B and B' respectively) that are approximately 0.579" OD. The bottom of each cartridge is a grating to which fine mesh stainless steel screen has been spot welded on the inside. At the top of each cartridge are separate heavy stainless steel retainer grating (C and C' for the primary and backup sections respectively). Fine-mesh stainless steel screen is spot-welded to the bottom of each grating. These gratings slip inside the sample cartridges and retain the sorbent bed in place. Alternatively, plugs of silanized glass wool may be used in place of these gratings.

The sampler is loaded as follows: first, the backup cartridge (B') is slipped into the sampler body. The backup cartridge rests on a land (D) at the bottom of the cylinder housing. A Teflon gasket (E') is inserted above the backup cartridge. The primary sorbent cartridge (B) is then inserted. Another Teflon gasket (E) is placed behind the front cartridge. Once inserted, the cartridges are held in place in the sampler body by a retainer tube (approximately 0.579" OD) (F) that compresses against the upper stainless steel retainer grating as shown. There are holes in the retainer tube (at I) and in the main body of the sampler (at H). As the retainer tube is inserted into the main sampler body, the holes on the retainer tube and on the main sampler body are aligned and a small threaded retainer key (H) is inserted through the hole in the outer sampler body and into the matching hole on the inner retainer tube. This arrangement locks the canisters into place and keeps the entire assembly tight.

Once sampling is completed, the sampler is returned to the laboratory for analysis. The sampler is disassembled by first removing the threaded retainer key. The entire assembly including the retainer cylinder, the primary backup sample cartridges and the Teflon gaskets are then removed by pushing the sample cartridges out of the sampler with a convenient tool (e.g., a solid rod) from the open end of the sampler body welded to the adaptor (A).

Each of the cartridges are then separately inserted into a 0.579" ID thermal desorber tube to which a land such as D of FIG. 11 has been welded. The cartridges would be inserted such that they rested atop the land. Each cartridge is then separately analyzed by placing the assembly inside a thermal desorber oven unit for analysis.

Although thermal desorption as the most desirable desorption procedure has been discussed, other techniques for recovering the solvent from the sorbent, e.g. solvent desorption or extraction with supercritical fluids, may also be used as appropriate.

Figure 13:
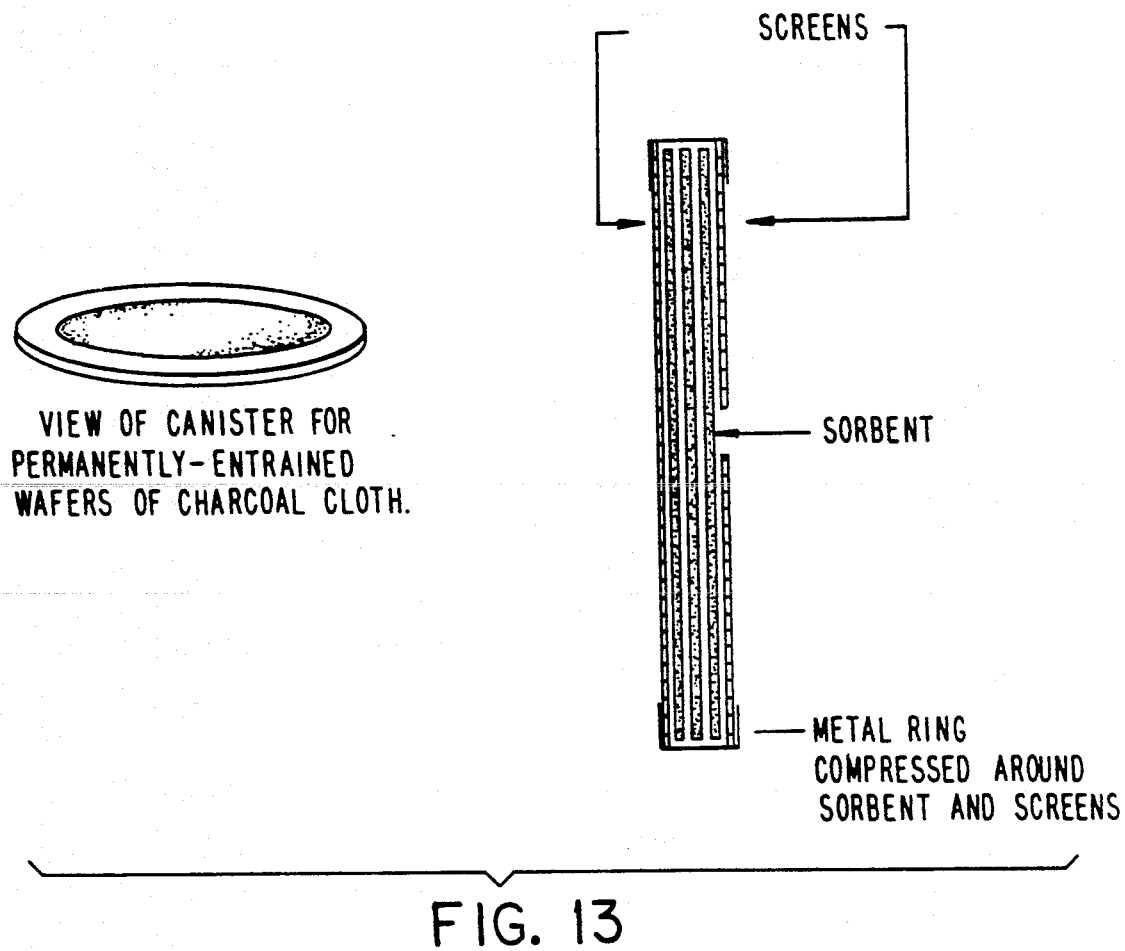
FIG. 13 is a schematic view of a mainstream sample canister that is primarily intended for permanently containing the charcoal cloth or granular sorbents.

Unlike some other sorbent containers, the container of FIG. 13 can be made so that it cannot be disassembled. It is primarily intended for use in an occupational health clinic where complaints regarding exposure may be substantiated, perhaps several days post-exposure by sampling a large volume of breath using such a container. Since the sorbent cannot be readily removed from the container for solvent desorption, it is preferred that the sample be desorbed by thermal means or by using supercritical fluids.

Figure 15:
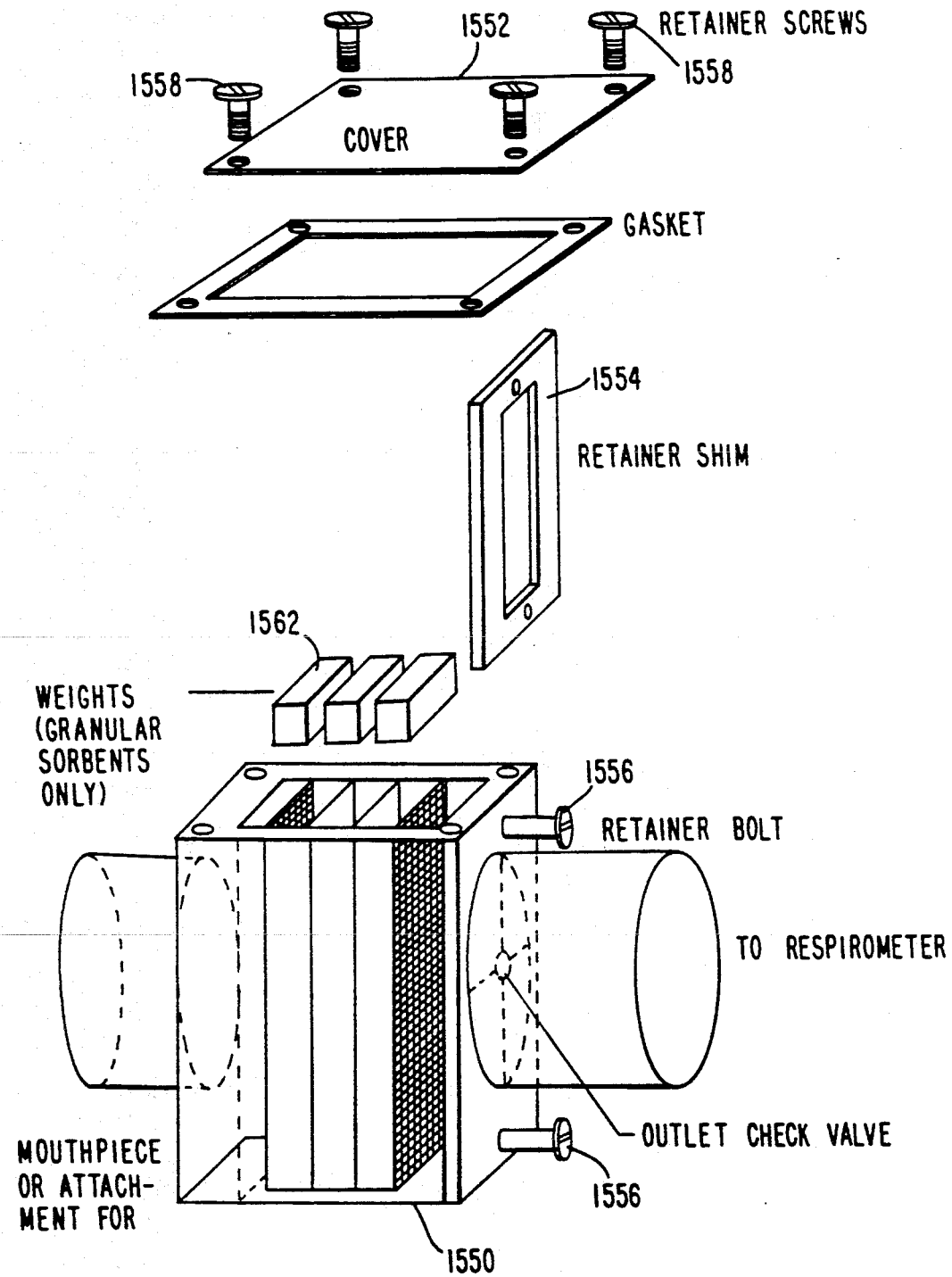
FIG. 15 is a schematic view of a square mainstream sample canister.

The canister 1550 of FIG. 15 can essentially replace canister 240 in FIG. 2. It is preferred that this canister be constructed of inert materials which do not absorb volatiles such as stainless steel, anodized aluminum, or PTFE (Teflon ®). Here the body of the sample canister 1550 does not have to be divided into threaded male and female components as do the canister of FIGS. 1, 2 and 3. Rather than separating the two halves of the canister to insert the sorbent container(s) such as part 412 in FIG. 4, the cover 1552 on the top of the sampling chamber is removed and individual sample containers inserted. A retainer shim 1554 has also been included in the sampler arrangement. For ease of viewing, this retainer shim 1554 is shown outside the body of the sampler. Alternatively, the shim 1554 may be permanently held in place at the outlet and of the body of the sampler using the retainer bolts shown. Its purpose is to seal the individual sample containers against one another during use. The sorbent containers are loosely inserted into the canister 1550. The two retainer bolts 1556, 1556 on the backside of the canister body are then tightened against the shim forcing it against the sorbent containers. This arrangement should also facilitate the recovery of the sorbent container from the canister, as the user would not need to forcibly remove tight fitting sample containers from the canister, but simply release the retainer shim 1554 and remove the sample containers. In addition, it allows ready use of oversized or multi-depth sample containers.

As shown in FIG. 15, the cover is mounted to the sampler body with screws 1558; a gasket 1560 is used to seal the cover with the body of cannister 1550. Alternatively, the cover 1552 may be mounted to the sampler body by sliding it in a track mounted to the top of that body or sealed in place with a clamp. A reason for this arrangement is to permit ready use of granular sorbents. The granular sorbent is compressed in place with the weights 1562 shown to prevent channeling through the sorbent bed during sampling. However, the sorbent container may also be used with charcoal such as charcoal cloth in three-wafer sections. In addition, this permits the use of double-size sorbent containers for granular sorbents weighted as necessary with oversize weights.

The arrangement has the further advantage of reducing waste of the charcoal cloth sorbent and of the fine mesh retainer screen. Cutting circular wafers of charcoal cloth or fine mesh screen from a rectangular roll of sheet stock does not allow all of that stock to be used whereas the use of square or rectangular wafers will.

Figure 16:
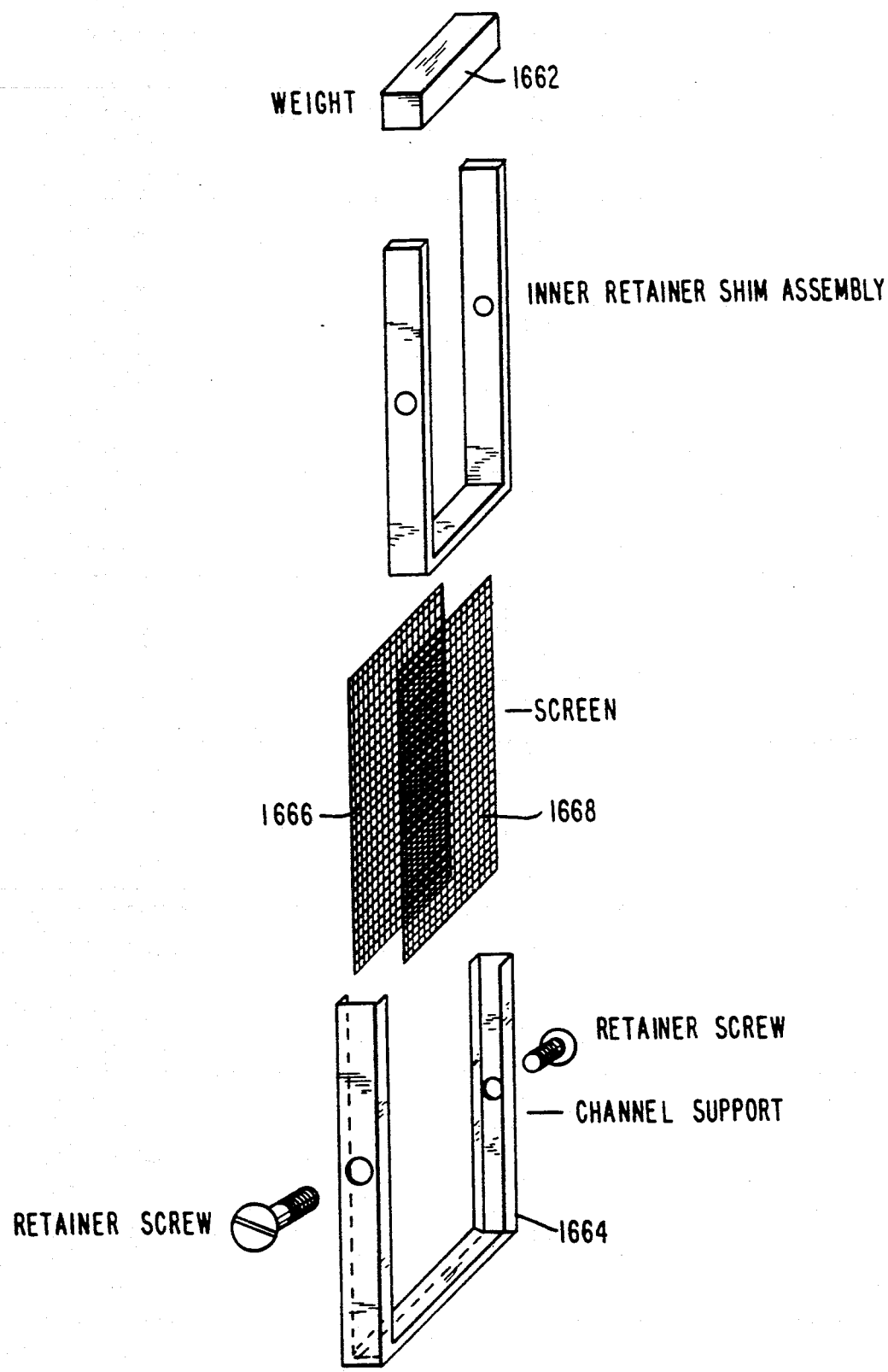
FIG. 16 shows the construction of a removable square container for granular sorbents.

The container channel support of FIG. 16 may be fabricated separately from stainless steel- or aluminum-channel stock. The front and back fine mesh stainless steel screens 1666, 1668 are approximately 40-mm square, giving approximately the same exposed surface area as that of the currently proposed 45 mm diameter wafers of charcoal cloth. These screens 1666, 1668 are inserted into the protruding arms of the channel support 1664. The inner retainer shim assembly 1654 is then forced, as shown FIG. 15, into the channel supports 1664 to retain the screen 1668 in place. In order to stabilize the assembly, the outer channel support may be spot welded or bolted to the inner retainer shim.

Figure 17:
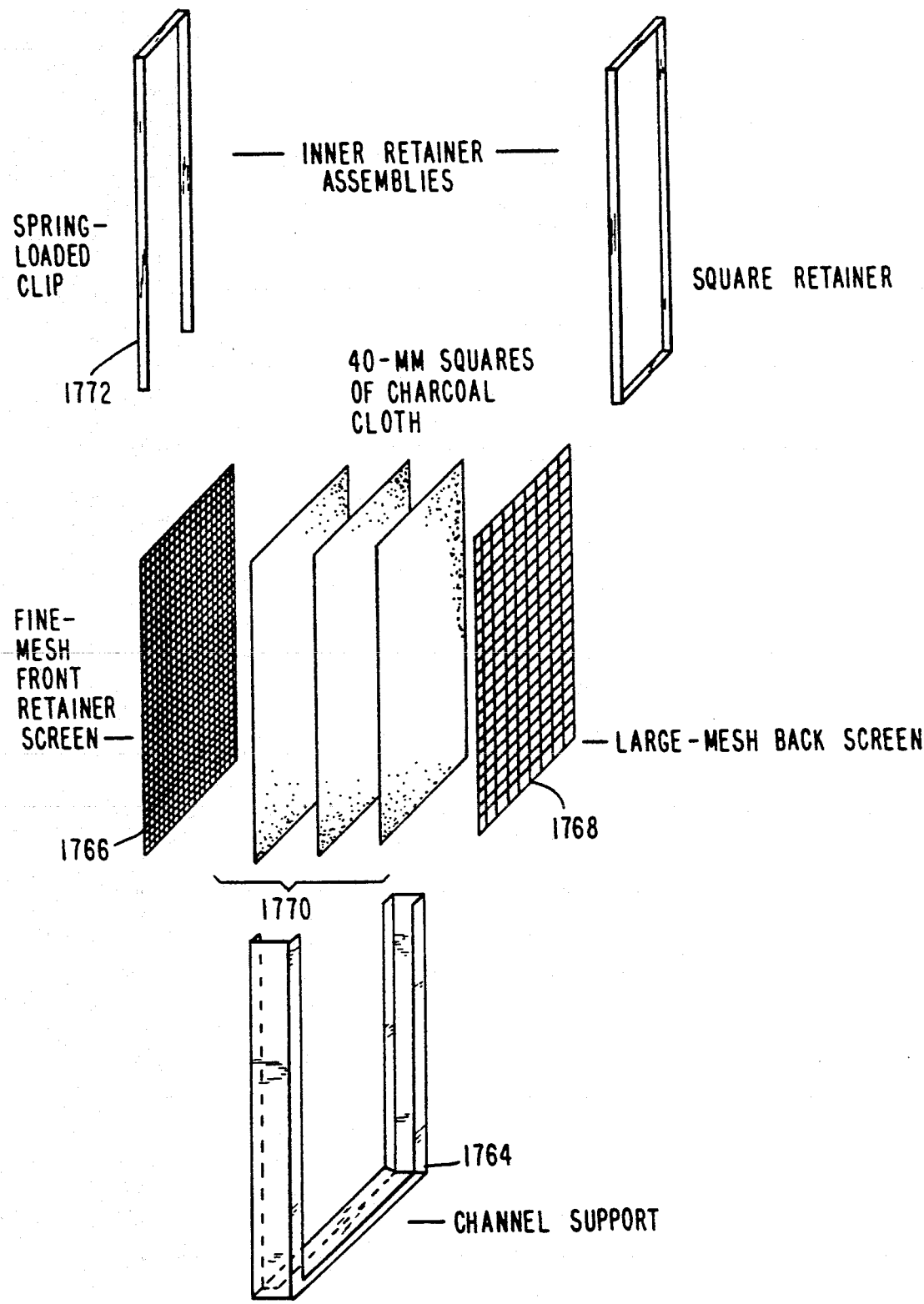
FIG. 17 shows the construction of a square container for use with removable charcoal cloth sorbents.

The container channel support 1764 of FIG. 17 is fabricated as described above for granular sorbents; however, it may not be as deep as the channel support 1664 since the charcoal wafers are very thin. The front fine-mesh stainless steel screen 1766 is inserted into the channel support. Typically, three 40 mm square wafers of the charcoal cloth are laid over the front fine mesh screen 1766 in the channel support 1764, followed by a large mesh backup screen 1768. A thin square inner shim assembly is then inserted over the large-mesh back screen to retain the sorbent assembly 1770 in place. Alternatively, a two-legged spring-loaded thin inner shim assembly 1772 may be used for this purpose; the two legs are compressed then inserted and allowed to expand to seal the bed in place.

One possible sampling configuration would involve three sample containers of the type described by FIG. 17 where the sample canister would contain front, middle and back sorbent sections of charcoal cloth wafers or wafers of other sorbent material. This arrangement finds use for high-vapor pressure analytes that migrate from one sorbent section to the next during storage because it permits the individual sorbent sections to be separated from one another immediately after sampling. Alternatively, it permits spacers such as thin 40 mm square sheets of stainless steel to be inserted between the three sorbent sections to minimize such migration. Another obvious configuration is assembled as above except that the entire sorbent bed is placed in a triple-depth channel support. First, the front fine mesh retainer screen is inserted, followed by the front charcoal cloth sorbent bed, a large mesh spacer screen, the middle charcoal cloth bed, another large-mesh spacer screen, and finally the backup charcoal cloth bed followed by the back large mesh screen, followed by the retainer clip.

Figure 18:
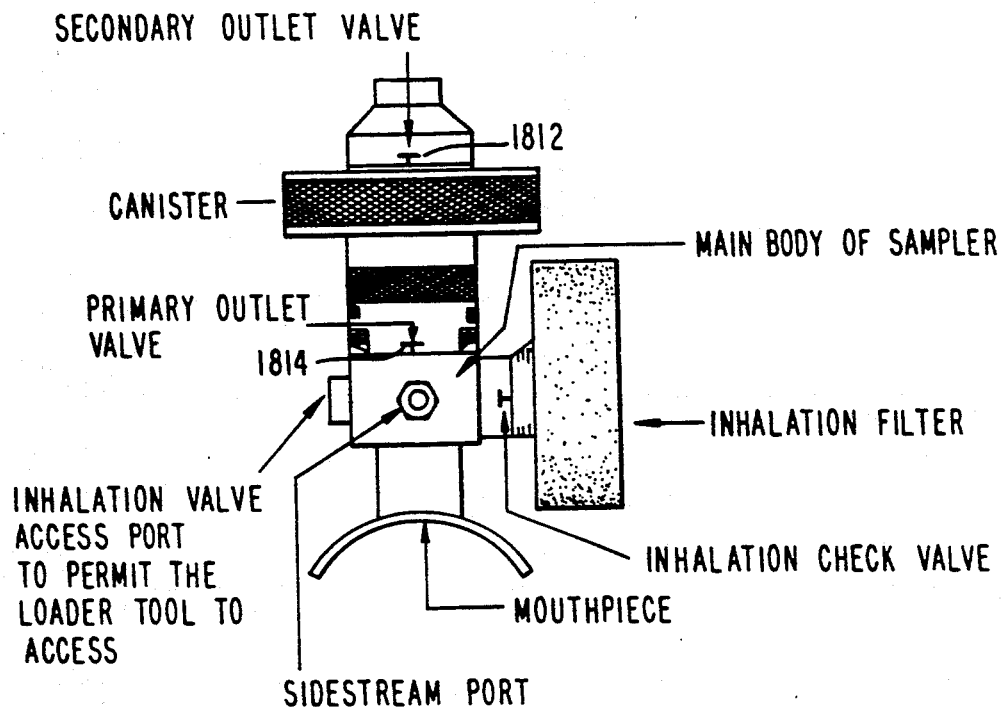
FIG. 18 shows a dose receiving sampler designed for the subject to use while exposed to the analyte gas. However, in order for the dose to be estimated the inhalation canister is first removed. Otherwise, this sampler may be used for mixed-expired sampling as the samplers described in FIGS. 1 and 2.
Figure 20:
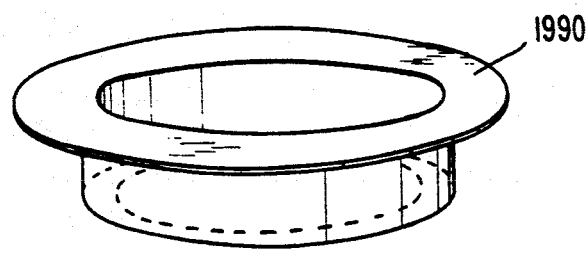
FIGS. 19 and 20 each show a sample canister with sorbent for alternate use in the system of FIG. 4.

Another variation on the sampler configuration is one which permits estimation of the total amount of analyte received by the subject. This is shown in FIG. 18 which lacks a filter capable of removing the analyte from the inhaled ambient air and is specifically designed to be used in an area of contaminated air. The contaminated air is inhaled through an inhalation check valve and exhaled through a canister of sorbent. To ensure that all the exhaled air and none of the inhaled or ambient air passes through the sorbent canister, at least one and preferably two check valves 1812, 1814 (one on each side of the canister) are added. The conduit leading from the mouthpiece may also optionally have an access port for sampling the air or replacing the inlet check valve(s).

The dose that a subject receives of a particular analyte can be calculated by measuring the total volume exhaled multiplied by the analyte concentration and the percent absorbed by the subject. The percentage absorbed can easily be calculated from the amount measured in the canister. From the dose absorbed per breath one can then determine the total dose absorbed by the subject and act accordingly. Air concentrations of various analytes are fair measures of one's exposure to gasses and volatile chemicals but they do not indicate the actual amount received. In accordance with the invention one finally has an easy, unobtrusive, and readily repeatable technique on demand to determine the estimated amount the body actually absorbed.

Figure 19:
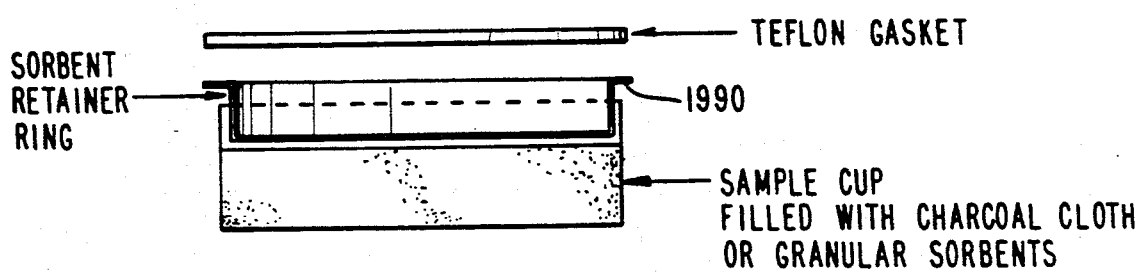

FIG. 19 shows a simple sorbent retainer ring 1990 that may replace part 404. The retainer may fit into the sample canister 412. At the bottom it engages the rear retainer screen 406 and at the top it engages the Teflon washer 402 in FIG. 4. Along with the toroidal weight, the retainer ring 1990 may also have a cutout to engage an anti-rotational lug in the sample canister. The system may use any particular sorbent or combination of sorbents.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A portable, through-flow breathing system for collecting breath samples from a human subject for subsequent determination of selected analyte content thereof, comprising:

a tubular body having a minimal volume compatible with having engageable first and second ends;

first conduit means for conveying through the tubular body the subject's essentially once-exhaled breath, said first conduit means fluidly communicating with said tubular body at a location intermediate said first and second ends;

second conduit means fluidly communicating with said first end of said tubular body, said second conduit means including air filtering means and selectively operable first valve means for admitting ambient air through said filtering means and into said tubular body when a subject inhales through said second conduit means; and third conduit means fluidly communicating with said second end of said tubular body, said third conduit means including low impedance, compact analyte collection means for concentrating a collected analyte for prolonged storage pending analysis thereof located therein and selectively operable second valve means for admitting the essentially once-exhaled breath from said tubular body into said sample collection means when the subject exhales through said first conduit means, said tubular body and said first, second and third conduit means being formed to be compact and lightweight in combination to facilitate convenient holding thereof by the human subject during use, and said first valve means being closed when said second valve means is open, and said second valve means being closed when said first valve means is open thereby ensuring sampling of only a through-flow of the subject's essentially once-exhaled breath.

2. The apparatus of claim 1, wherein:
said tubular body has a substantially "T-shaped" configuration.

3. The apparatus of claim 1, wherein:
said first, second and third conduit means each have a respective longitudinal axis, the longitudinal axis of said first conduit means being disposed at respective predetermined angles to the corresponding axes of said second and third conduit means.

4. The apparatus of claim 3, wherein:
said predetermined angles each comprise at least 90 degrees.

5. The apparatus of claim 1, wherein:
said first and second valves in said second and third conduit means each comprise a check valve.

6. The apparatus of claim 5, wherein:
each of said check valves is removable from its respective conduit means.

7. The apparatus of claim 1, wherein:
said sample collection means comprises a container including at least one bed of a selected sorbent material.

8. The apparatus of claim 7, wherein:
said at least one bed of sorbent material comprises a bed of charcoal cloth for collection of an analyte.

9. The apparatus of claim 1, wherein:
said tubular body includes an opening and further comprises connection means provided at said opening for connecting thereat to means for carrying out sidestream sampling in known manner.

10. The apparatus of claim 1 wherein:
at least one of the sample collection means and the air filtering means comprises a removable canister containing a selected sorbent.

11. The apparatus of claim 10, wherein:
the sorbent comprises charcoal cloth.

12. A method for measuring the concentration of a selected analyte in a sample of essentially once-exhaled breath provided by a subject, comprising the steps of:
prefiltering air inhaled by the subject from the ambient atmosphere with a filter capable of significantly removing such of the selected analyte as is present in the ambient air, to thereby ensure accurate subsequent measurement of the concentration of the selected analyte in the sample comprising the subject's essentially once-exhaled breath;
passing the breath sample directly through a selected sorbent example capable of sorbing the selected analyte therefrom, wherein the sorbent element is formed and disposed to present a low impedance flow passage to the breath sample passed therethrough;
determining the volume of the breath sample from which analyte has been sorbed by the sorbent example;
desorbing the sorbed analyte from the sorbent element;
measuring an amount of the selected analyte desorbed from the sorbent; and
determining a concentration of the selected sorbent in the determined volume of essentially once-exhaled breath provided by the subject.

13. The method of claim 12, wherein:
the breath sample contains air from more than one exhalation.

14. A method for measuring the concentration of a selected analyte in a multi-breath sample of essentially once-exhaled breath from a subject, comprising the steps of:
passing a sample comprising multiple breaths, each being essentially once-exhaled, from the subject directly through a selected sorbent capable of retaining at least one analyte present in said sample;
desorbing the at least one retained analyte from the sorbent;
measuring a volume of said breath sample; and
thereby determining a concentration of the desorbed analyte in the multiple breaths provided by the subject.

15. The method of claim 14, comprising the further step of:
prefiltering air inhaled by the subject from the ambient atmosphere with a filter capable of significantly removing the at least one selected analyte therefrom to ensure accurate measurement of the concentration of such of the at least one selected sorbed analyte as was present in the sample of the subject's substantially once-exhaled breath.

16. The method of claim 12 or 14, wherein: the analyte is desorbed by thermal desorption.

17. The method of claim 12 or 14, wherein: the breath sample is an alevolar breath sample.

18. Apparatus for collecting from a subject a sample of essentially once-exhaled breath containing a selected analyte, for subsequent determination of a concentration of the selected analyte in the sampled exhaled breath, comprising:
a tubular conduit having a first opening to receive a flow-through of essentially once-exhaled breath from the subject, a second opening and a third opening to permit inhalation of ambient air by the subject; and
means for collecting a sample of the selected analyte from said essentially once-exhaled breath, connected to said second opening,
wherein the second and third openings contain respective first and second valve means to permit only said essentially once-exhaled breath to pass through the sample collection means.

19. The apparatus of claim 18, wherein:
the sample collection means contains a sorbent capable of retaining at least the selected analyte.

20. The apparatus of claim 18, wherein:
said first and second valve means comprise respective check valves.

21. The apparatus of claim 20, wherein:
said sample collection means has a check valve located at least upstream thereof to minimize collection of ambient inhaled air with said exhaled breath.

* * * * *